(12) United States Patent
Kobayashi

(10) Patent No.: US 7,957,503 B2
(45) Date of Patent: Jun. 7, 2011

(54) MEDICAL BREAST-IMAGE CAPTURING APPARATUS

(75) Inventor: Masaaki Kobayashi, Shimotsuke (JP)

(73) Assignee: Canon Kabushiki Kaisha, Tokyo (JP)

( * ) Notice: Subject to any disclaimer, the term of this patent is extended or adjusted under 35 U.S.C. 154(b) by 58 days.

(21) Appl. No.: 11/869,660

(22) Filed: Oct. 9, 2007

(65) Prior Publication Data
US 2008/0089471 A1   Apr. 17, 2008

(30) Foreign Application Priority Data
Oct. 11, 2006   (JP) ................. 2006-277382

(51) Int. Cl.
*A61B 6/04* (2006.01)
(52) U.S. Cl. .......................... 378/37; 378/209
(58) Field of Classification Search ............ 378/37, 378/208–209
See application file for complete search history.

(56) References Cited

U.S. PATENT DOCUMENTS

| 6,298,114 | B1 | 10/2001 | Yoda |
| 2002/0057758 | A1* | 5/2002 | Stark ................. 378/37 |
| 2004/0111801 | A1* | 6/2004 | Marin et al. ............ 5/621 |

FOREIGN PATENT DOCUMENTS

JP   06-510930   12/1994

* cited by examiner

*Primary Examiner* — Hoon Song
(74) *Attorney, Agent, or Firm* — Canon U.S.A., Inc. I.P. Division

(57) ABSTRACT

A medical breast-image capturing apparatus includes an aperture member for exposing a breast of a test subject. To perform adequate breast cancer screening, the aperture member has a noncircular shape, is arranged to be replaceable with another aperture member, or has a variable opening. Another medical breast-image capturing apparatus includes a pressure-reducing device for reducing a pressure in a hollow section in which a breast is exposed.

5 Claims, 5 Drawing Sheets

MEDICAL BREAST-IMAGE CAPTURING APPARATUS

BACKGROUND OF THE INVENTION

1. Field of the Invention

The present invention relates to a medical breast-image capturing apparatus which acquires a medical image of a breast of a test subject using radiation such as X-rays, ultrasonic waves, MRI, etc.

2. Description of the Related Art

An improved X-ray mammography apparatus capable of photographing a breast of a patient (test subject) while the patient is in a prone position is discussed in, for example, Japanese Patent No. 2691073.

In the mammography apparatus described in Japanese Patent No. 2691073, photographing is carried out while the patient lies on a bed in a prone position. The bed functions as a support platform and is provided with a breast-receiving aperture through which the patient inserts a breast. The breast that hangs down is exposed to X-rays while it is pressed between compression plates. In this apparatus, the patient is not required to be in an unnatural position and can relax during the procedure, so that accurate measurement can be performed while suppressing the patient's movement during the photographing process.

However, similar to the known mammography technique, it is necessary to press the patient's breast with the compression plates in the above-described structure. This can give considerable pain to the patient. Therefore, many patients have a negative impression about mammography that the procedure involves pain.

In the above-described apparatus, an area that can be photographed in a single process is limited because of the shape of the photographing subject. Therefore, a plurality of photographing processes must be performed for each breast, and the above-mentioned process of pressing the breast must be performed each time. In addition, since information obtained by the photographing process is two-dimensional data, photographing must be performed in a plurality of directions to determine X, Y, and Z coordinates of a lesion necessary for guiding a biopsy needle.

In the above-described apparatus, photographing is performed while the patient is in a prone position and the patient's breast hangs down. In general, when a breast is divided into four quadrants, breast cancer is often found in an upper outer area, that is, in an upper area near the shoulder. Therefore, the photographing area is required to cover this area. In the known mammography method in which photographing is performed while a patient is in an upright position, an image of deep tissue in the upper outer area of the breast can be obtained by photographing this area in a medical lateral oblique direction.

However, when a breast that is inserted through a substantially circular aperture is photographed, it is relatively difficult to pull out the upper outer portion of the breast compared to an outer lower portion thereof. In addition, when the breast inserted through the aperture is pressed between the compression plates while the patient is in a prone position as described in Japanese Patent No. 2691073, rear breast tissue can be pushed away from the X-ray irradiation area by the edges of the compression plates.

In the above-described known apparatus, the breast-receiving aperture is substantially circular and has a fixed size and shape. However, patients have different body sizes. Therefore, it is difficult to set a necessary photographing area for each patient using the hole with a fixed size and shape. As a result, there is a risk that the area of a portion presented in the photographing area will vary.

SUMMARY OF THE INVENTION

The present invention is directed to a medical breast-image capturing apparatus with an improved positional relationship between a photographing system including an X-ray tube and an X-ray detector and a breast, which is a photographing subject. The improvement in the positional relationship adequately increases the photographing area and allows photographing of the breast over a large area.

The present invention is also directed to a medical breast-image capturing apparatus capable of photographing, irrespective of individual differences between breasts of patients, breast tissue in an upper outer area near the shoulder where breast cancer is often found. In general, this area can easily be hidden in a blind spot outside the photographing area.

According to an aspect of the present invention, a medical breast-image capturing apparatus includes an aperture member configured to expose a breast of a test subject and a detector configured to acquire a medical image of the breast exposed by the aperture member. The aperture member has an opening having a noncircular shape such that tissue in an upper outer area of the breast is exposed in the opening.

Further features of the present invention will become apparent from the following description of exemplary embodiments with reference to the attached drawings.

DESCRIPTION OF THE EMBODIMENTS

Embodiments of the present invention will be described below with reference to the accompanying drawings.

First Embodiment

Figure 1:
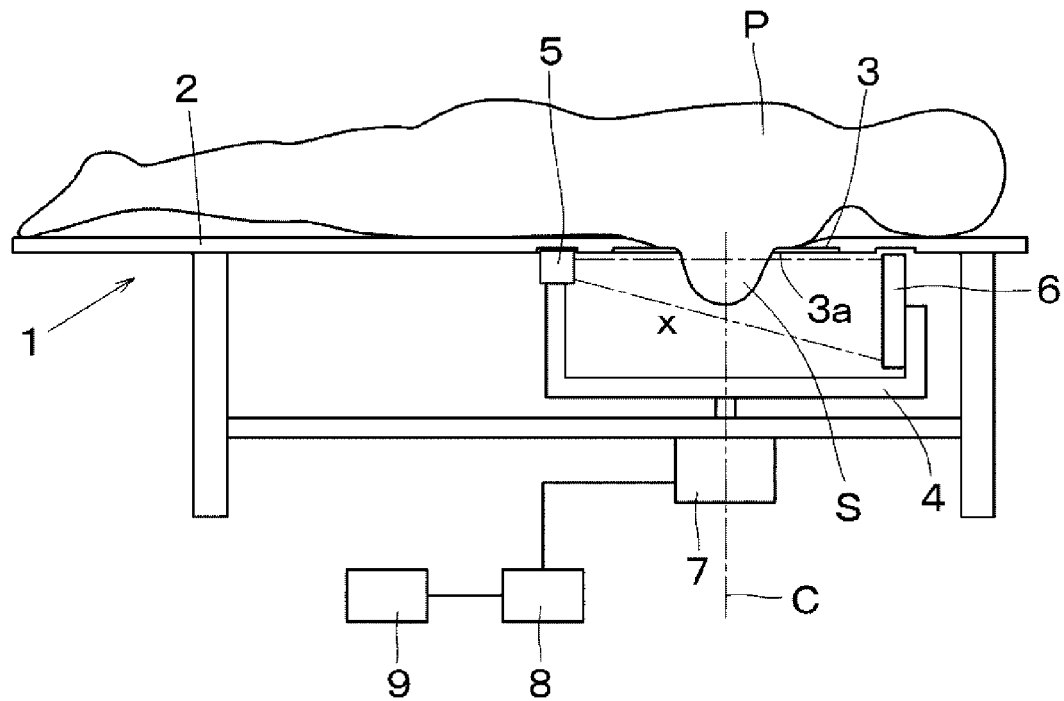
FIG. 1 shows a structure of a first embodiment.

FIG. 1 shows the structure of an X-ray CT apparatus according to a first embodiment. Referring to FIG. 1, a bed 1 is used for photographing a breast of a patient P. The bed 1 includes a top plate 2 that functions as a support plate for supporting the patient P in a prone position. The top plate 2 has an aperture member 3 through which a breast of the patient P is inserted. The aperture member 3 has an opening 3a and is rotatable relative to the top plate 2 about the center of the opening 3a. The aperture member 3 is gradually tapered from the top plate 2 to the opening 3a.

An arm 4 is placed under the aperture member 3. The arm 4 rotates about a rotational axis C that extends through the center of the opening 3a in a vertical direction. An X-ray tube unit 5 and an X-ray detector 6 are respectively held at one end and the other end of the arm 4. The X-ray detector 6 includes an X-ray sensor for converting X-rays into electrical signals. The arm 4 is driven by a rotary driver 7. The rotary driver 7 is controlled on the basis of commands from a controller 8 that controls each component. The controller 8 has a CPU and a memory for storing control programs to be executed by the CPU. The CPU executes the control programs and thereby carries out processes according to the present embodiment.

An image processing unit 9 receives image data output from the X-ray detector 6 and performs image processing, such as a reconstruction process (sectional image generation), in response to commands output by the controller 8.

Figure 2A:
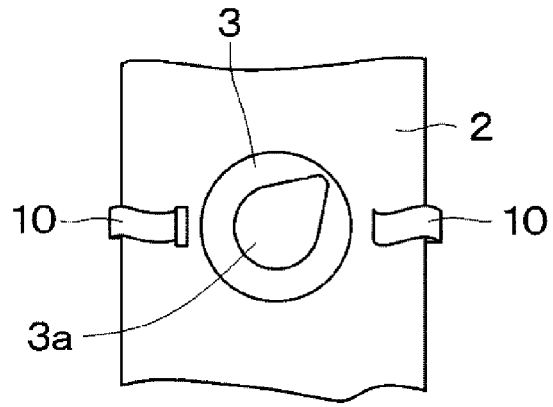
FIGS. 2A and 2B are plan views of an aperture member.
Figure 2B:
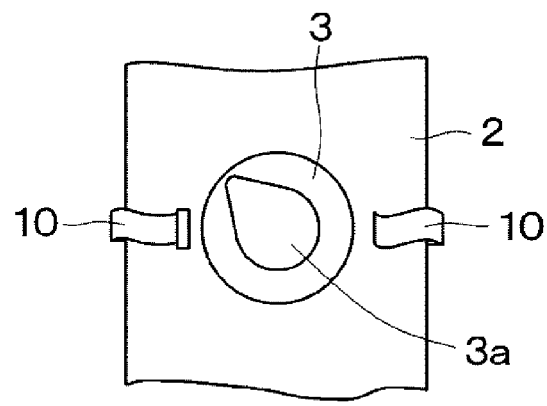

FIGS. 2A and 2B are plan views of the aperture member 3 provided on the top plate 2. FIG. 2A illustrates the setting for photographing a right breast of the patient P, and FIG. 2B illustrates the setting for photographing a left breast of the patient P. The opening 3a is shaped like a liquid drop, and has a circular portion and a triangular portion. The aperture member 3 is rotatable, and therefore can be used for photographing both the left and right breasts using the settings shown in FIGS. 2A and 2B.

Belts 10 for restraining the patient P are provided on either side of the top plate 2 at positions near the aperture member 3. In the photographing process, the belts 10 are joined together at the back of the patient P in a prone position. Accordingly, the patient P is pressed against the top plate 2 and a peripheral portion of the breast, that is, a photographing subject S, is pressed against a peripheral edge of the aperture member 3. Therefore, the breast in the opening 3a is pushed downward into a photographing area and hangs down due to gravity.

According to the present embodiment, due to the effects of not only the weight of the breast itself but also the pressing force applied by the belts 10, tissue surrounding the breast can also be placed in the photographing area. In addition, since the patient P is restrained by the belts 10, movement of the patient P is suppressed during the photographing process. Thus, undesirable influences on the image reconstruction process can be reduced.

In the photographing process, the patient P lies on the top plate 2 in a prone position with breasts facing down. At this time, the patient P can place one of the breasts into the opening 3a without discomfort since a gently curved surface extends between the top plate 2 and the opening 3a in the aperture member 3.

When the aperture member 3 is set as shown in FIG. 2A, the patient P places the right breast into the opening 3a. Accordingly, the right breast and a portion in the upper outer area of the breast that extends from the breast to the right shoulder are inserted trough the opening 3a having the triangular portion. Thus, tissue in the breast and the portion in the upper outer area of the breast, where breast cancer is often found, are exposed in the photographing area below the aperture member 3.

According to the present embodiment, it is not necessary to press the breast between compression plates. Therefore, tissue is prevented from being moved away by the pressure applied thereto and the portion projecting downward through the opening 3a can be directly subjected to photographing.

When the left breast of the patient P is to be photographed, an operator rotates the aperture member 3 to the left until the triangular portion of the opening 3a reaches the upper left position as shown in FIG. 2B. In this state, the patient P places the left breast into the opening 3a. Accordingly, similar to the right breast, tissue in the left breast and the portion in the upper outer area of the breast, where breast cancer is often found, are exposed in the photographing area below the aperture member 3.

The aperture member 3 can also be structured such that the aperture member 3 is detachable from the top plate 2. In such a case, the aperture member 3 is turned over and attached to the top plate 2 again so that the aperture member 3 can be used for both of the left and right breasts as in the above-described structure in which the aperture member 3 is rotatable. In addition, a plurality of aperture members 3 having openings 3a with different sizes, shapes, positions, etc., can be prepared so that a suitable aperture member 3 can be selected depending on the body shape of each patient P. In such a case, before the patient P lies on the top plate 2 in a prone position, the aperture member 3 can be placed directly on the breast of the patient P to confirm whether or not a desired photographing area can be obtained while the patient P is in a suitable position.

If the aperture member 3 does not fit the breast, the aperture member 3 can be replaced with another aperture member 3. Then, the photographing area is checked again. Then, the suitable aperture member 3 is set to the bed 1 and the patient P lies on the bed 1. Thus, a process of optimizing the photographing area, which is difficult to perform while the patient P is lying in a prone position, can be easily performed.

In the present embodiment, the breast, which is the photographing subject S extending downward through the opening 3a in the aperture member 3, is photographed using the X-ray detector 6, which is a two-dimensional planar detector. The X-ray tube unit 5 and the X-ray detector 6 are slowly rotated around the breast by one turn, so that a tomographic image that can be effectively used for diagnosis is obtained. In the procedure, it is not necessary to press the breast between compression plates, and burden on the patient P is reduced. Therefore, the patient P can relax during the photographing process, so that degradation in accuracy caused by the patient's movement can be reduced.

Figure 3A:
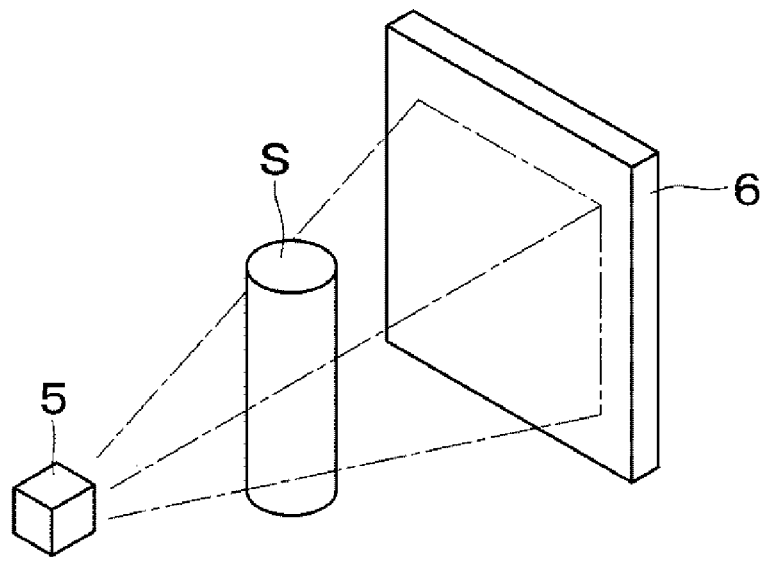
FIGS. 3A, 3B, and 3C are diagrams illustrating an X-ray irradiation area.
Figure 3B:
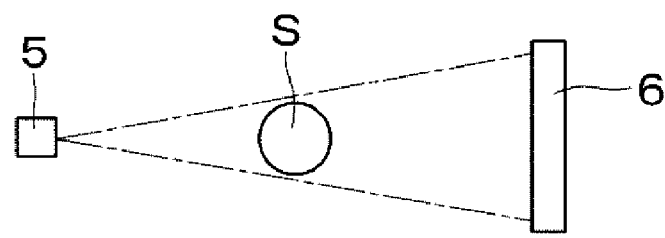
Figure 3C:
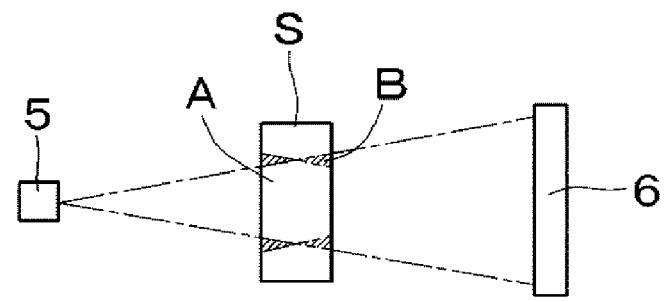

A conical X-ray beam that expands in vertical and horizontal directions is emitted from the X-ray tube unit 5 toward the X-ray detector 6, as shown in FIG. 3A. FIGS. 3B and 3C are a plan view and a side view, respectively, corresponding to FIG. 3A. In FIGS. 3A, 3B, and 3C, the photographing subject S is schematically shown as a column.

The X-ray tube unit 5 and the X-ray detector 6 rotate around the photographing subject S while irradiating the photographing subject S with the conical X-ray beam. At this time, because of the expansion of the X-ray beam, an area A where the X-ray beam is constantly incident on the photographing subject S and an area B where the X-ray beam is intermittently incident on the photographing subject S are generated. Information of 360° is obtained in the area A, so that an accurate image can be reconstructed after the data is acquired. In comparison, in the area B, the accuracy is reduced because information cannot be obtained in a certain angular range. In particular, the accuracy is largely reduced if the distance between the X-ray tube unit 5 and the X-ray detector 6 is small.

In the process of photographing a breast with the X-ray CT apparatus according to the present embodiment, the state of X-ray irradiation must be set such that tissue in a rear area close to pectoral muscle in the breast, which is the photographing subject S, is placed outside the area B. The photographing area can be made as large as possible by reducing the area B. Therefore, the X-ray tube unit 5 is arranged such that the top face of the conical X-ray beam shown in FIG. 1 is perpendicular to the rotational axis C in the entire angular range of 360°. In other words, the top face of the effective image pickup area formed by the rotation is arranged to be parallel to the top plate 2, thereby making the maximum use of information obtained by the X-ray irradiation. As a result, unnecessary exposure of the patient P to the X-ray can be reduced.

The X-ray tube unit 5 and the X-ray detector 6 are positioned as high as possible, so that an area extremely close to the opening 3a in the aperture member 3 can be placed within the photographing area. For example, as shown in FIG. 1, the X-ray tube unit 5 and the X-ray detector 6 can be arranged on concentric circles centered on the rotational axis C below the bottom surface of the top plate 2. The arrangement angles and the aperture are set such that the top face of the conical X-ray beam x is perpendicular to the rotational axis C.

Thus, the breast that hangs through the opening 3a in the aperture member 3 can be photographed over the area extending to the upper end thereof. A desired photographing area can be obtained by adequately setting the opening 3a.

The X-ray tube unit 5 and the X-ray detector 6 are retained by the arm 4 and are rotated about the rotational axis C by the rotary driver 7. In the X-ray irradiation process, the controller 8 outputs an X-ray exposure signal for controlling an X-ray emitting device. Accordingly, the X-ray beam x is emitted from the X-ray tube unit 5. The X-ray detector 6 is controlled in synchronization with the exposure and receives the X-ray beam x that passes through the breast. Image data corresponding to the received X-ray beam x is stored in, for example, the memory included in the controller 8. After the image data of the breast in the range of 360° is obtained, a three-dimensional image is reconstructed by the image processing unit 9.

Second Embodiment

Figure 4:
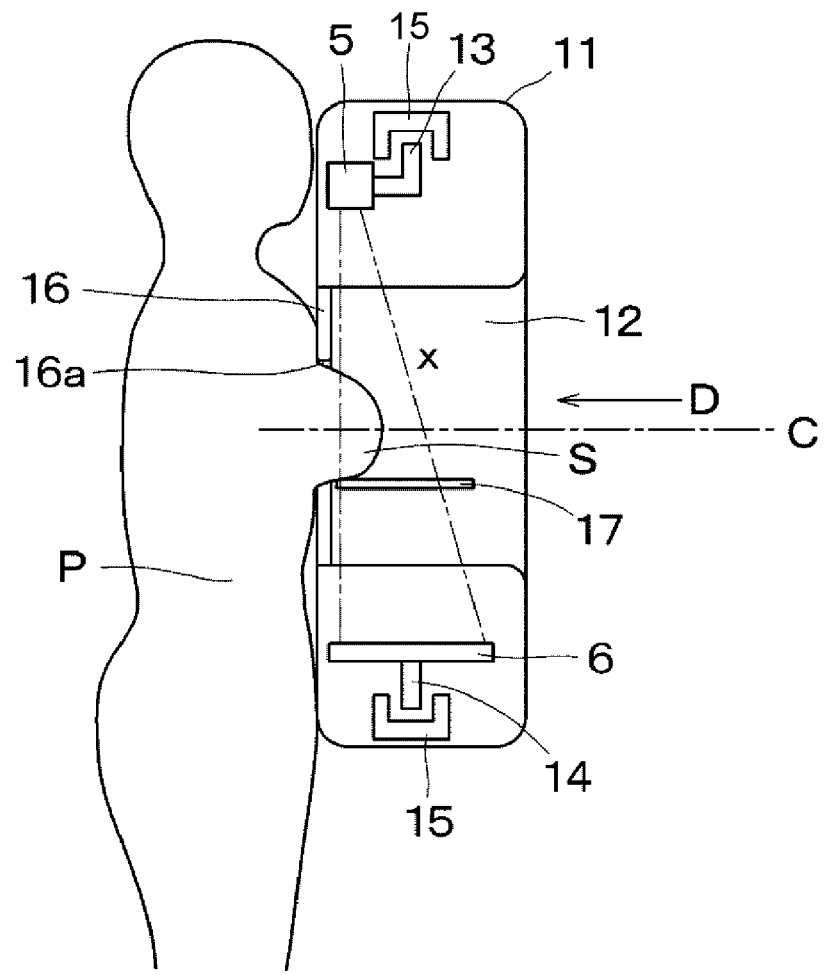
FIG. 4 shows a structure of a second embodiment.

FIG. 4 shows a structure of a second embodiment. Referring to FIG. 4, an X-ray tube unit 5 and an X-ray detector 6 are placed in a donut-shaped frame body 11 that is retained by a main frame (not shown). Photographing can be performed while a patient P is in an upright position by placing a breast, which is a photographing subject S, along a horizontal central axis C of the frame body 11. A central space 12 around the central axis C of the frame body 11 functions as a photographing area. The size of the frame body 11 can be reduced by limiting the photographing subject to breasts.

The X-ray tube unit 5 and the X-ray detector 6 are retained by retaining members 13 and 14, respectively, in the frame body 11. The retaining members 13 and 14 rotate about the central axis along the inner periphery of an annular guide 15. Thus, data of the breast, which is the photographing subject S, in the range of 360° can be obtained.

An aperture member 16 having an opening 16a is attached to the frame body 11 so as to cover a hole in the front of the frame body 11. Similar to the first embodiment, the aperture member 16 can either be rotatable or detachable. Also in the second embodiment, an end face of an X-ray beam emitted from the X-ray tube unit 5 is set to be parallel to the aperture member 16, so that a portion of the breast near the opening 16a can be reliably photographed.

The breast projecting into the central space 12 through the opening 16a in the aperture member 16 can hang down due to its own weight. Therefore, a breast-supporting plate 17 can be placed in the space 12. The breast-supporting plate 17 is arranged to be constantly positioned within the irradiation area of the X-ray beam while the X-ray beam rotates, and is made of a material with low X-ray absorption. To suppress movement of the patient P, belts or the like are provided on the front side of the frame body 11 to retain the patient P while the patient P is pressed against the frame body 11.

Thus, effects similar to those obtained by the first embodiment can also be obtained in the second embodiment. In addition, since photographing is performed while the patient P is in an upright position, positioning of the patient P can be facilitated. Therefore, the structure of the second embodiment can be used in a situation in which many patients P are to be subjected to the photographing process. In addition, the installation space can be reduced, so that the apparatus can be used in a limited space, such as in a vehicle.

The X-ray tube unit 5 and the X-ray detector 6 are slowly rotated about the central axis C of the frame body 11 by one turn, so that a tomographic image can be obtained. Therefore, it is not necessary to use complex, expensive components having a high-speed rotation mechanism or a mechanism for supplying electric power during rotation.

In the second embodiment, an operator can check the state of the patient P whose breast is positioned so as to project through the opening 16a in the aperture member 16, that is, the position of the breast to be photographed, from the position denoted by D. In addition, the aperture member 16 can be easily adjusted or replaced with another aperture member by causing the patient P to temporarily move away from the apparatus. The aperture member 16 can also be provided with a mechanism for directly changing the size of the opening 16a.

Figure 5:
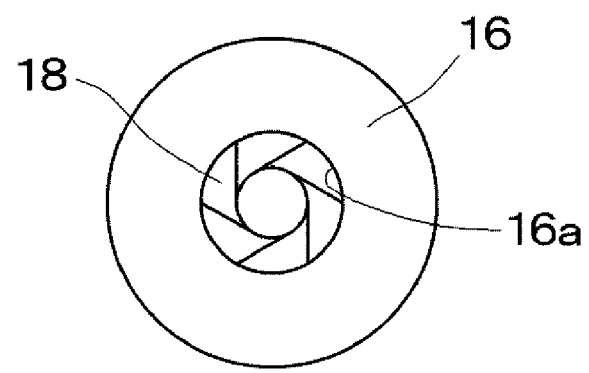
FIG. 5 is a front view of another aperture member.

FIG. 5 shows an example of the aperture member 16 viewed from the patient P. The aperture member 16 has a plurality of diaphragm blades 18 along the opening 16a. The diaphragm blades 18 have grooves that can be moved with pins so as to change the size of the opening 16a. Although the mechanism is somewhat complex, this example is advantageous in that it is not necessary to detach the aperture member 16.

Figure 6:
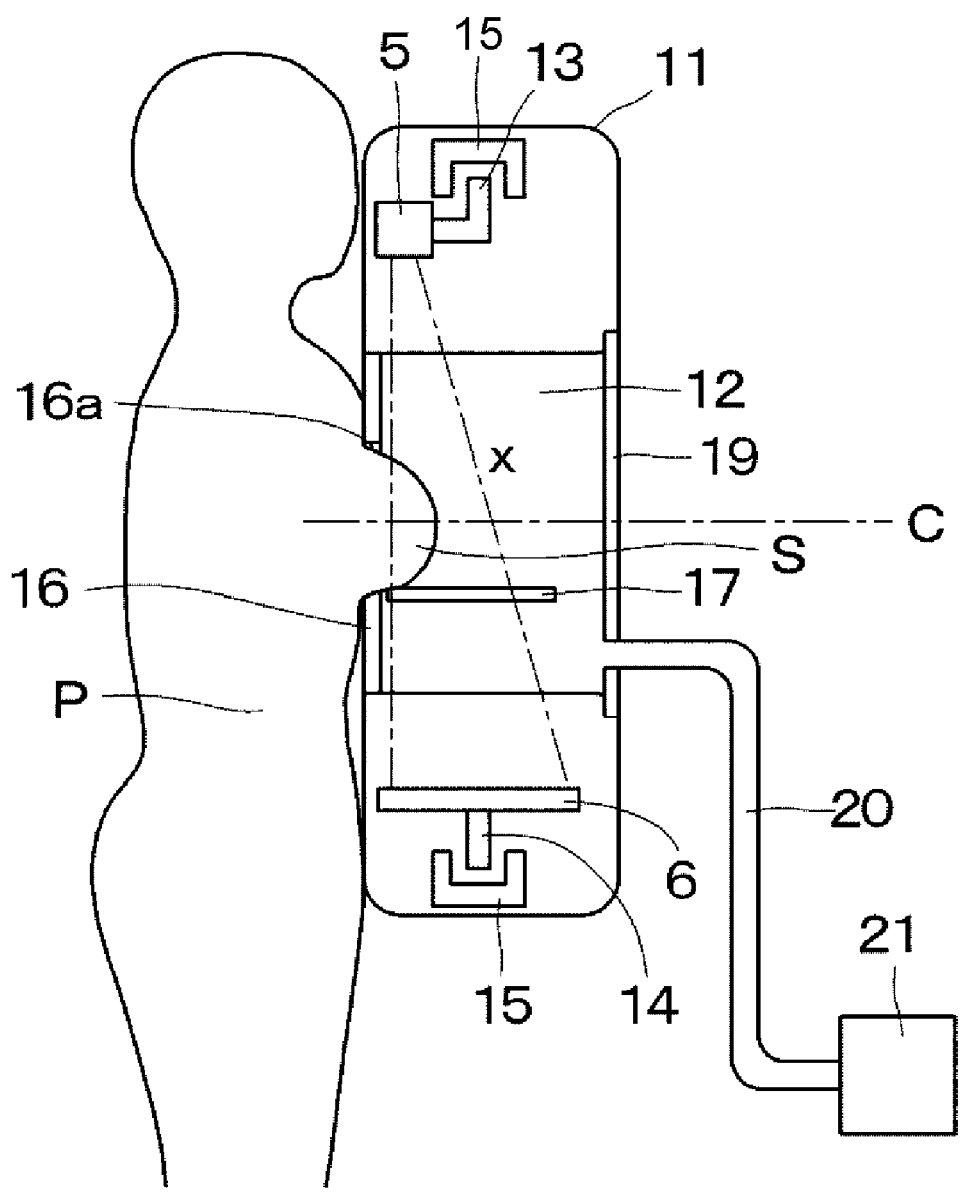
FIG. 6 shows a structure of a modification.

FIG. 6 shows a modification of the second embodiment. In FIG. 6, a transparent cover 19 is provided on a rear side of the central space 12 in the frame body 11. The central space 12 is sealed except for the opening 16a formed in the aperture member 16. The cover 19 has a suction hole that is connected to a vacuum pump 21 with a tube 20.

When the patient P presses the breast against the aperture member 16, the central space 12 becomes airtight. In this state, the vacuum pump 21 is activated so as to reduce the pressure in the central space 12. The breast receives not only the pressing force applied by the above-described belts but also the suction force applied due to pressure reduction. As a result, tissue around the breast is sucked in through the opening 16a and is placed within the photographing area.

The vacuum suction mechanism according to the second embodiment can also be used in the first embodiment. However, this mechanism can be more effectively used in the frame structure for performing photographing while the patient P is in an upright position, as in the second embodiment.

In addition to CT apparatuses and common radiographic image capturing apparatuses, the aperture members 3 and 16 can also be used in medical image capturing apparatuses for capturing medical images using ultrasonic waves, MRI, etc.

Third Embodiment

Figure 7:
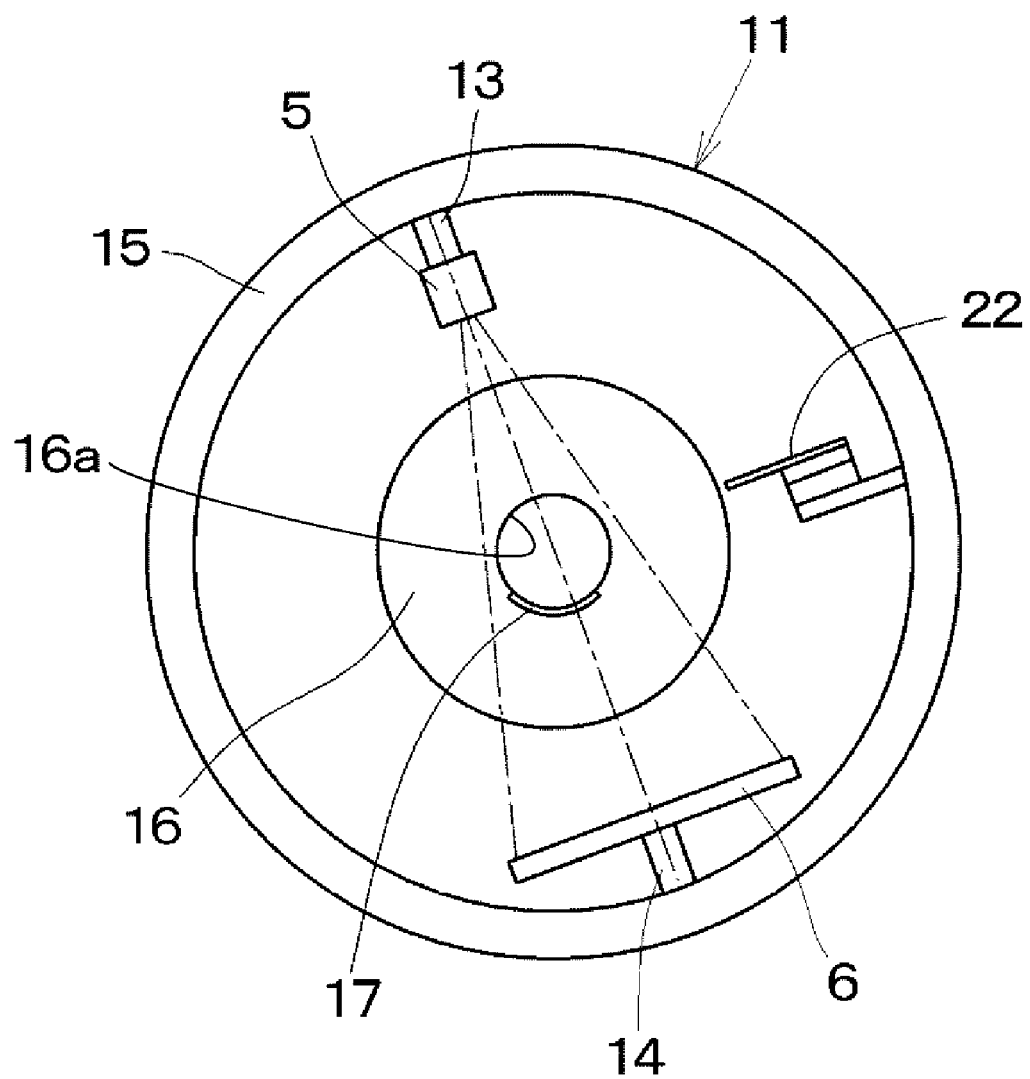
FIG. 7 is a sectional view illustrating a structure of a third embodiment.

FIG. 7 is a sectional view of a frame body 11 taken along a plane perpendicular to a rotational axis according to a third embodiment. A biopsy device 22 is attached to a guide 15 together with an X-ray tube unit 5 and an X-ray detector 6 such that the biopsy device 22 can move along the guide 15. Accordingly, a needle can be inserted into the breast at an arbitrary angle to extract a biopsy sample.

In the third embodiment, X, Y, and Z coordinates of a lesion that are necessary for guiding the biopsy needle can be obtained by a single photographing process. Since the biopsy device 22 is provided in the frame body 11, a biopsy process can be performed after the X-ray photographing process without changing the state of the breast. As a result, time required for the test and burden on the patient P can be reduced.

In the above-described embodiments, X-ray is explained as an example of radiation. However, other kinds of radiations can also be used.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-277382 filed Oct. 11, 2006, which is hereby incorporated by reference herein in its entirety.

What is claimed is:

1. A medical breast-image capturing apparatus comprising:
  a support plate for supporting a patient;
  the support plate including an aperture member, the aperture member having an opening through which a breast of the patient is inserted;
  the opening of the aperture member having a predetermined shape, and the aperture member being configured to be rotatable relative to the support plate about the center of the opening; and
  a photographing unit including an X-ray tube unit that rotates on a rotational axis around the opening,
  wherein the rotational axis passes through the center of the opening, and
  wherein the aperture member is turned over so as to be attached to and detached from the top plate so that the predetermined shape of the opening can be set to alternately receive the left breast and the right breast of the patient.

2. The medical breast-image capturing apparatus according to claim 1, wherein the aperture member is rotatable so that the predetermined shape of the opening can be set to alternately receive the left breast and the right breast of the patient.

3. The medical breast-image capturing apparatus according to claim 1, wherein the predetermined shape is a liquid-drop-like shape that has a circular portion and a triangular portion.

4. The medical breast-image capturing apparatus according to claim 1, wherein, during imaging of breast of the patient, it is not necessary to press the breast of the patient between compression plates.

5. The medical breast-image capturing apparatus according to claim 1, wherein the support plate includes a belt for fixing a subject near the opening of the aperture member.

* * * * *